United States Patent
Ahmad et al.

(10) Patent No.: US 9,874,620 B2
(45) Date of Patent: Jan. 23, 2018

(54) LOW FIELD MAGNETIC RESONANCE IMAGING (MRI) SCANNER FOR CARDIAC IMAGING

(71) Applicant: Ohio State Innovation Foundation, Columbus, OH (US)

(72) Inventors: Rizwan Ahmad, Columbus, OH (US); Lee C. Potter, Riverlea, OH (US); Adam Rich, Columbus, OH (US); Orlando P. Simonetti, Columbus, OH (US); Samuel T. Ting, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 15/013,316

(22) Filed: Feb. 2, 2016

(65) Prior Publication Data

US 2016/0232690 A1    Aug. 11, 2016

Related U.S. Application Data

(60) Provisional application No. 62/112,223, filed on Feb. 5, 2015.

(51) Int. Cl.
*G06T 11/00* (2006.01)
*G06T 5/00* (2006.01)
(Continued)

(52) U.S. Cl.
CPC ............ *G01R 33/48* (2013.01); *A61B 5/0044* (2013.01); *A61B 5/055* (2013.01); *G06T 2207/10088* (2013.01); *G06T 2207/30048* (2013.01)

(58) Field of Classification Search
CPC ............ G06T 11/005; G06T 2211/424; G06T 2207/10088; G06T 2207/30048;
(Continued)

(56) References Cited

U.S. PATENT DOCUMENTS

| 2007/0198203 A1* | 8/2007 | Kimura | ................ G06T 5/002 |
| | | | 702/85 |
| 2010/0142841 A1* | 6/2010 | Vaidya | ................ G01R 33/56 |
| | | | 382/254 |

(Continued)

OTHER PUBLICATIONS

Afonso MV et al. An augmented Lagrangian approach to the constrained optimization formulation of imaging inverse problems. 17th IEEE Conference on Image Processing, Hong Kong, 4169-4172, 2010.

(Continued)

*Primary Examiner* — Jon Chang
(74) *Attorney, Agent, or Firm* — Meunier Carlin & Curfman LLC

(57) ABSTRACT

A low-cost magnetic resonance imaging (MRI) apparatus that may be used for, e.g., Cardiac MRI (CMR). CMR is a clinical imaging tool that can investigate a wide range of cardiac conditions by exploring changes in the anatomy, physiology, or dynamics of the heart. The applications of CMR include, but are not limited to, the evaluation of congenital heart disease, coronary heart disease, ischemic heart disease, cardiac masses, the pericardium, cardiomyopathy, hibernating myocardium, and valvular and ventricular function. Generally, the MRI apparatus is a low-field (~0.5 T) system equipped with a high-end data processing unit (DPU) to enable the implementation of structure aware (SA) recovery in clinically relevant times.

15 Claims, 7 Drawing Sheets

(51) Int. Cl.
G06T 7/00 (2017.01)
G01R 33/48 (2006.01)
A61B 5/055 (2006.01)
A61B 5/00 (2006.01)

(58) Field of Classification Search
CPC ..... A61B 5/0033; A61B 5/0044; A61B 5/055; G01R 33/48
USPC .......................................................... 382/131
See application file for complete search history.

(56) References Cited

U.S. PATENT DOCUMENTS

2014/0376794 A1* 12/2014 Dumoulin .......... G01R 33/5611
 382/131
2015/0374237 A1* 12/2015 Hu ......................... A61B 5/055
 600/413

OTHER PUBLICATIONS

Candes, Emmanuel J., et al. "Compressed sensing with coherent and redundant dictionaries." Applied and Computational Harmonic Analysis 31.1 (2011): 59-73.

Combettes, Patrick L., and Jean-Christophe Pesquet. "A Douglas—Rachford splitting approach to nonsmooth convex variational signal recovery." IEEE Journal of Selected Topics in Signal Processing 1.4 (2007): 564-574.

Lustig, Michael, David Donoho, and John M. Pauly. "Sparse MRI: The application of compressed sensing for rapid MR imaging." Magnetic resonance in medicine 58.6 (2007): 1182-1195.

Rangan, S. (Jul. 2011). Generalized approximate message passing for estimation with random linear mixing. In Information Theory Proceedings (ISIT), 2011 IEEE International Symposium on (pp. 2168-2172). IEEE.

Vila, J. P., & Schniter, P. (2013). Expectation-maximization Gaussian-mixture approximate message passing. IEEE Transactions on Signal Processing, 61(19), 4658-4672.

Walsh, David O., Arthur F. Gmitro, and Michael W. Marcellin. "Adaptive reconstruction of phased array MR imagery." Magnetic Resonance in Medicine 43.5 (2000): 682-690.

Ziniel, J., Rangan, S., & Schniter, P. (Aug. 2012). A generalized framework for learning and recovery of structured sparse signals. In 2012 IEEE Statistical Signal Processing Workshop (SSP) (pp. 325-328). IEEE.

Ziniel, J., & Schniter, P. (2013). Dynamic compressive sensing of time-varying signals via approximate message passing. IEEE transactions on signal processing, 61(21), 5270-5284.

* cited by examiner

LOW FIELD MAGNETIC RESONANCE IMAGING (MRI) SCANNER FOR CARDIAC IMAGING

CROSS-REFERENCE TO RELATED APPLICATION

This application claims priority to U.S. Provisional Patent Application No. 62/112,223, filed Feb. 5, 2015, entitled "Low Field Magnetic Resonance Imaging (MRI) Scanner for Cardiac Imaging," which is incorporated by reference in its entirety.

BACKGROUND

Cardiac magnetic resonance (CMR) is a noninvasive imaging tool with a wide range of cardiovascular applications. Apart from CMR, two common modalities for routine, non-invasive, diagnostic cardiac imaging are echocardiography (cardiac ultrasound) and nuclear SPECT. Although other imaging modalities exist for every clinical application of CMR, no single modality that can match the comprehensiveness of CMR. Despite the unique and broad applicability of CMR, it is underutilized due to its relatively poor cost effectiveness. As such, there is almost no market for Cardiac MRI (CMR) machines.

Conventionally, it is understood that signal-to-noise ratio (SNR) improves with increasing magnetic field strength. Over the past two decades, the trend has been to design MRI scanners with higher and higher field strengths in order to increase SNR. The increase in SNR is traded for improved spatial and temporal resolutions and reduced acquisition times. Increasing the magnetic field strength, however, requires larger magnets with more challenging specifications. Therefore, higher field MRI systems tend to be considerably more expensive and thus less cost effective for applications, such as CMR, that do not significantly benefit from the higher field strength. In addition, higher magnetic fields may negatively affect image quality, patient safety, and comfort.

SUMMARY

Cardiac magnetic resonance (CMR) is a clinical imaging tool that can investigate a wide range of cardiac conditions by exploring changes in the anatomy, physiology, or dynamics of the heart. Disclosed herein are systems and methods for reconstructing image data. The method may include acquiring multichannel k-space data; determining a noise power of the k-space data; determining coil-sensitivity maps; initializing values of relative weights (regularization strengths) applied to each subdictionary used to model an image; iteratively minimizing a weighted $l_1$-norm of image representation in subdictionaries in accordance with the relative weights while constraining the residual norm of the data-fidelity term based on the measured noise power; within each iteration, updating the relative weights of subdictionaries based on the subdictionary-specific maximum likelihood fitting of coefficient distributions with a Laplacian; and outputting the reconstructed images upon convergence.

In accordance with other aspects, an MRI machine is described having a low-field (e.g., 0.5 T) magnet. This lower field strength targets a new market for MRI and cardiac imaging. For example, such a device has a price point competitive with echocardiography machines and SPECT cameras.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

DETAILED DESCRIPTION

Unless defined otherwise, all technical and scientific terms used herein have the same meaning as commonly understood by one of ordinary skill in the art. Methods and materials similar or equivalent to those described herein can be used in the practice or testing of the present disclosure. While implementations will be described for remotely accessing applications, it will become evident to those skilled in the art that the implementations are not limited thereto, but are applicable for remotely accessing any type of data or service via a remote device.

The present disclosure is directed to a low-cost magnetic resonance imaging (MRI) apparatus that may be used for, e.g., Cardiac MRI (CMR). CMR is a clinical imaging tool that can investigate a wide range of cardiac conditions by exploring changes in the anatomy, physiology, or dynamics of the heart. The applications of CMR include, but are not limited to, the evaluation of congenital heart disease, coronary heart disease, ischemic heart disease, cardiac masses, the pericardium, cardiomyopathy, hibernating myocardium, and valvular and ventricular function.

Example Environment

Figure 1:
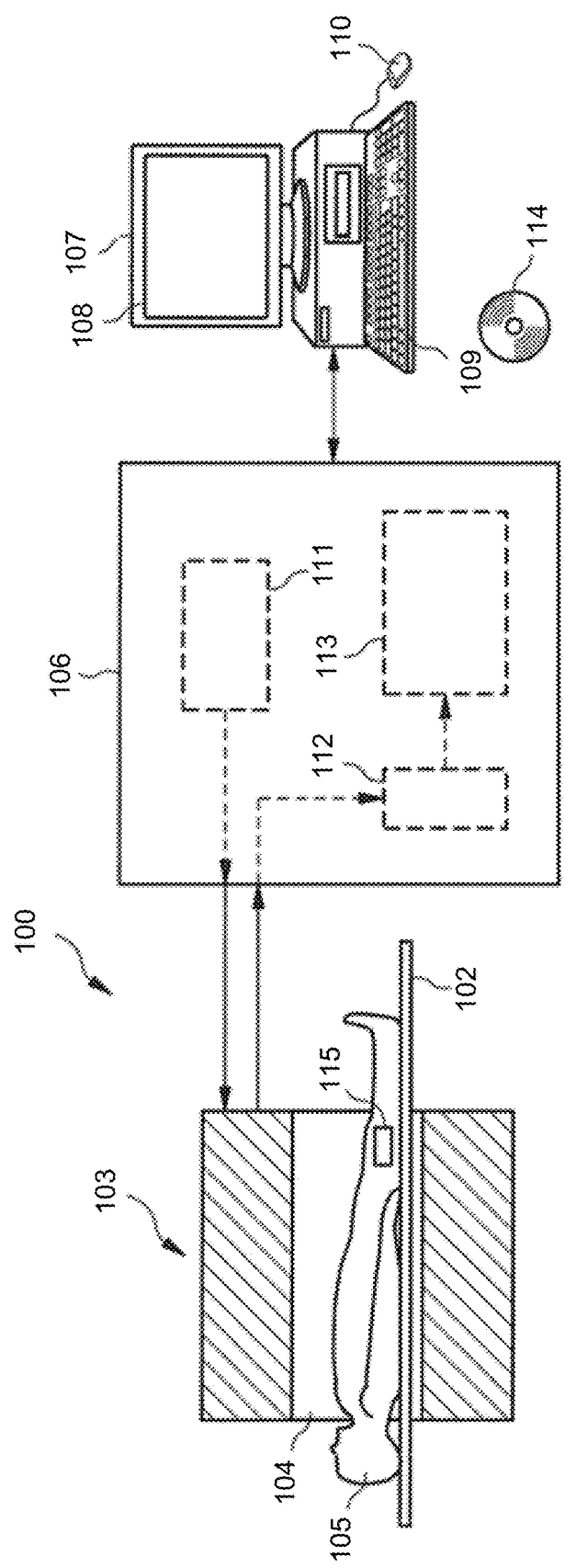
FIG. 1 is a diagram of a structure of a magnetic resonance imaging (MRI) apparatus according to an exemplary embodiment of the present invention.

FIG. 1 is a view illustrating a structure of an example magnetic resonance imaging (MRI) apparatus 100 that may be used to acquire image data. Generally, the MRI apparatus 100 is a low-field (~0.5 T) system equipped with a high-end data processing unit (DPU) to enable the implementation of structure aware (SA) recovery in clinically relevant times. The DPU is comprised of multiple GPUs running a Gadgetron framework, which was developed at the National Heart, Lung, and Blood Institute. The SA recovery methods are based on Bayesian inference where the structure in the image is expressed probabilistically, as a set of priors or conditional priors. For implementation of SA recovery, fast iterative image recovery methods based on Generalized Approximate Message Passing (GAMP) are employed, yielding fast algorithms with self-tuning parameters. Details of an operational flow and example SA recovery are provided below with reference to FIG. 2.

In addition, for a Bayesian approach, the entropy of the posterior probability may be computed to quantify confidence in the recovery of each pixel. For a non-Bayesian approach, a separate sensitivity analysis may be performed to create a confidence map. The confidence map may enable a clinician to de-emphasize areas within an image where uncertainty is above a threshold.

The MRI apparatus 100 includes a scanner 103 that generates magnetic fields used for the MR examination within a measurement space 104 having a patient table 102. In accordance with the present disclosure, the scanner 103 may include a wide bore 70 cm superconducting magnet having a field strength of approximately 0.5 Tesla (T).

A controller 106 includes an activation unit 111, a receiver device 112 and an evaluation module 113. During a phase-sensitive flow measurement, MR data are recorded by the receiver device 112, such that MR data are acquired in, e.g., a measurement volume or region 115 that is located inside the body of a patient 105. The MRI apparatus 100 may include an 18 coil array (e.g., arranged as two 3×3 grids); support parallel imaging using SPIRiT, GRAPPA, SENSE, VISTA, AMP, FISTA, SCoRE, and/or Bayesian Inference; and perform analog-to-digital conversion (ADC) at a gantry of the MRI apparatus 100.

An evaluation module 113 prepares the MR data such that they can be graphically presented on a monitor 108 of a computing device 107 and such that images can be displayed. In addition to the graphical presentation of the MR data, a three-dimensional volume segment to be measured can be identified by a user using the computing device 107. The computing device may include a keyboard 109 and a mouse 110. The computing device may include a Xeon central processing unit (CPU) or better; 16 GB of random access memory (RAM); Multi-GPU, K20 or Titan Z reconstruction hardware; support DiCOM 3.0; and support simultaneous scan and reconstruction.

Software for the controller 106 may be loaded into the controller 106 using the computing device 107. Such software may implement a method(s) to process data acquired by the MRI apparatus 100, as described below. It is also possible the computing device 107 to operate such software. Yet further, the software implementing the method(s) of the disclosure may be distributed on removable media 114 so that the software can be read from the removable media 14 by the computing device 107 and be copied either into the controller 106 or operated on the computing device 107 itself.

As would now be understood by one of skill in the art, the MRI apparatus 100 having a smaller 0.5 T magnet would cost less (e.g., require less shielding and a have a lower cost gradient assembly), be easier to construct, be physically smaller, weigh less and have lower power requirements than the larger MRI apparatuses, which follow current trends. As such, the MRI apparatus 100 may be installed locations where the larger MRI apparatuses cannot. The MRI apparatus 100 is also safer, as it has a smaller 5-G region (if actively shielded), a reduced chance smaller chance of objects flying to the magnet, induces a smaller torque to metallic implants (if not actively shielded), has a reduced specific absorption rate (SAR—by square of field strength), and reduced heating of implanted devices. Further, the MRI apparatus 100 creates less electrohemodynamic distortion of ECG signal, reduces susceptibility and chemical shift artifacts, generates smaller main field (B0) and transmit field (B1) inhomogeneity, and has smaller spatial variation of flip angles. The MRI 100 provides for greater patient comfort with a wider, shorter bore and lesser acoustic noise.

The MRI apparatus 100 provides several imaging advantages. For example, the reduced SAR allows for higher flip angles for trueFISP based sequences, which results to higher contrast-to-noise ratios (CNR). The MRI apparatus 100 also provides for shorter tissue T1's in non-contrast enhanced scans, increased relaxivity of contrast agents at lower field, use of trueFISP and EPI in new applications (perfusion, flow, LGE, etc.), and reduced artifacts surrounding implanted metallic devices. While the MRI apparatus 100 having a lower field strength may provide lower SNR, the SNR decreases approximately linearly from 1.5 T to 0.5 T. This can be offset by using higher flip angles (lower SAR), a shorter native T1 and by use of TrueFISP for applications not possible at higher field strength due to B0 inhomogeneties.

Thus, described above is a lower field-strength MRI machine for use in CMR (and other) applications.

Structure Aware (SA) Data Processing Overview

As noted above, structure aware (SA) data processing methods may be used to recover images acquired by the MRI apparatus 100. SA methods can recover stable images from highly undersampled data, alleviating typical SNR requirements and providing the potential for high quality imaging at low field strength. In addition, unlike static MRI, CMR, which is primarily a dynamic imaging method, includes the added dimension of time; this brings additional structure that can be exploited by SA methods.

SA imaging is a computationally intensive technique and relies on modeling of the MRI acquisition process. However, these models are more accurate at lower field strengths due to improved field homogeneity, thereby countering the loss in SNR at lower field. As such, the present disclosure builds upon a confluence of computational power, innovative SA reconstruction methods, and low field operation provide a novel paradigm for cost effective MRI.

Generally, the SA recovery of the acquired image series is posed as a Bayesian inference problem. To exploit the spatial structure of CMR, sparsity is enforced by promoting Bernoulli-Gaussian mixture (BGM) density on the wavelet coefficients of the image series. In addition, to uniquely utilize the dynamics in CMR, the slowly varying support of the wavelet coefficients across time is modeled as a Markov chain and the frame-to-frame correlation among the coefficients as Gauss-Markov process. The Bayesian inference for the above mentioned structured-sparsity in CMR is realized using computationally efficient turbo Generalized Massage Passing (turbo-GAMP) algorithm. To further accelerate the reconstruction process, turbo-GAMP may be implemented on a Gadgetron framework, as noted above. The above mentioned recovery procedure is named as CMR-AMP.

The reduced levels of field inhomogeneity-related artifacts at low field imply that most of the imperfection in low-field data is from additive white noise and not from model mismatch. Therefore, at low field, the lack of departure from ideal physics leverages itself to utilize advantages of CMR-AMP that cannot be fully realized at high-field. First, CMR-AMP can provide voxel-wise variance of the posterior probability. This variance map expresses the certainty in the recovery of each voxel, providing an extra layer of confidence for the image recovery at low-field. The recovery of variance of the posterior probability relies on the assumption that all the imperfection in the data arises from additive noise and not from model-mismatch, which is not the case at high field. Second, CMR-AMP can be self-tuned, where all the tuning parameters—including on the ones that define structure in CMR—are recovered via an expectation-maximization (EM) procedure. Again, EM recovery relies, in part, on the assumption of additive white noise, which is a more realistic assumption at low field.

Example Implementation

Below is an example implementation using a parameter-free recovery method, called Sparsity Adaptive Compressive Recovery (SCoRe), that models the image using a sparse representation in a union of subdictionaries, and that learns and exploits a non-uniform level of sparsity across subdictionaries.

MR images, like natural images, possess a rich structure that admits sparse representation under multiple, disparate transforms. For this reason, redundant dictionaries are routinely used to express and exploit structure in MR images. For MRI, two common choices of redundant dictionary include: (i) the undecimated wavelet transform (UWT) and (ii) the union of a total variation transform and the discrete wavelet transform. When using a redundant dictionary, however, the level of sparsity may vary across different groups of atoms, i.e., across "subdictionaries."

Therefore, using the same thresholding rule across subdictionaries may not yield acceptable results. For MRI, it is typical to formulate image reconstruction as an optimization problem of the form:

$$\underset{x}{\operatorname{argmin}} \ \|\Psi x\|_1^1 \ \text{such that} \ \|y - \Phi x\|_2^2 \leq \delta, \quad (1)$$

where $\Phi$ is the measurement matrix that employs sensitivity encoding and Fourier undersampling, $\Psi$ is a redundant dictionary, x is the image to be recovered, y is the measured data, and $\delta$ is an upper bound on the $l_2$ norm of the measurement noise, which can be estimated from a noise-only scan.

To allow for varying levels of sparsity at the subdictionary level, the problem in Eq. 1 may be generalized to:

$$\hat{x} = \underset{x}{\operatorname{argmin}} \sum_{i=1}^{D} \lambda_i \|\Psi_i x\|_1^1 \ \text{such that} \ \|y - \Phi_x\|_2^2 \leq \delta, \quad (2)$$

where $\Psi_i$ represents one of D subdictionaries, and $\lambda_i$ acts as a relative weight on the $i^{th}$ subdictionary and thus determines the extent of soft thresholding on $\Psi_i x$. From the perspective of unconstrained optimization, Eq. 2 can be viewed as a compound regularization,[2] with $\lambda_i$ determining the relative strength of the $i^{th}$ regularization term.

For MRI, the values of $\lambda_i$ are often selected by the user. In SCoRe, $\lambda_i$ is iteratively estimated by maximizing the likelihood function $\mathcal{L}(\lambda_i|\Psi_i \hat{x})$, where $\hat{x}$ is the previous image estimate. For an i.i.d. Laplacian prior on $\Psi_i \hat{x}$, maximizing the log-likelihood function yields $$\lambda_i = kN / \Sigma_{j=1}^{N} |[\Psi_i \hat{x}]_j|, \quad (3)$$

where $[\Psi_i \hat{x}]_j$ is the $j^{th}$ coefficient of $\Psi_i \hat{x}$ and N is the total number of coefficients in $\Psi_i \hat{x}$. Here, k=1 for real $\Psi_i \hat{x}$, and k=2 for complex $\Psi_i \hat{x}$. The implementation of SCoRe includes inner iterations to solve Eq. 2 using Douglas-Rachford splitting and outer iterations (Eq. 3) to update $\lambda_i$.

For the data presented herein, the number of outer and inner iterations may be 16 and 12, respectively.

Figure 2:
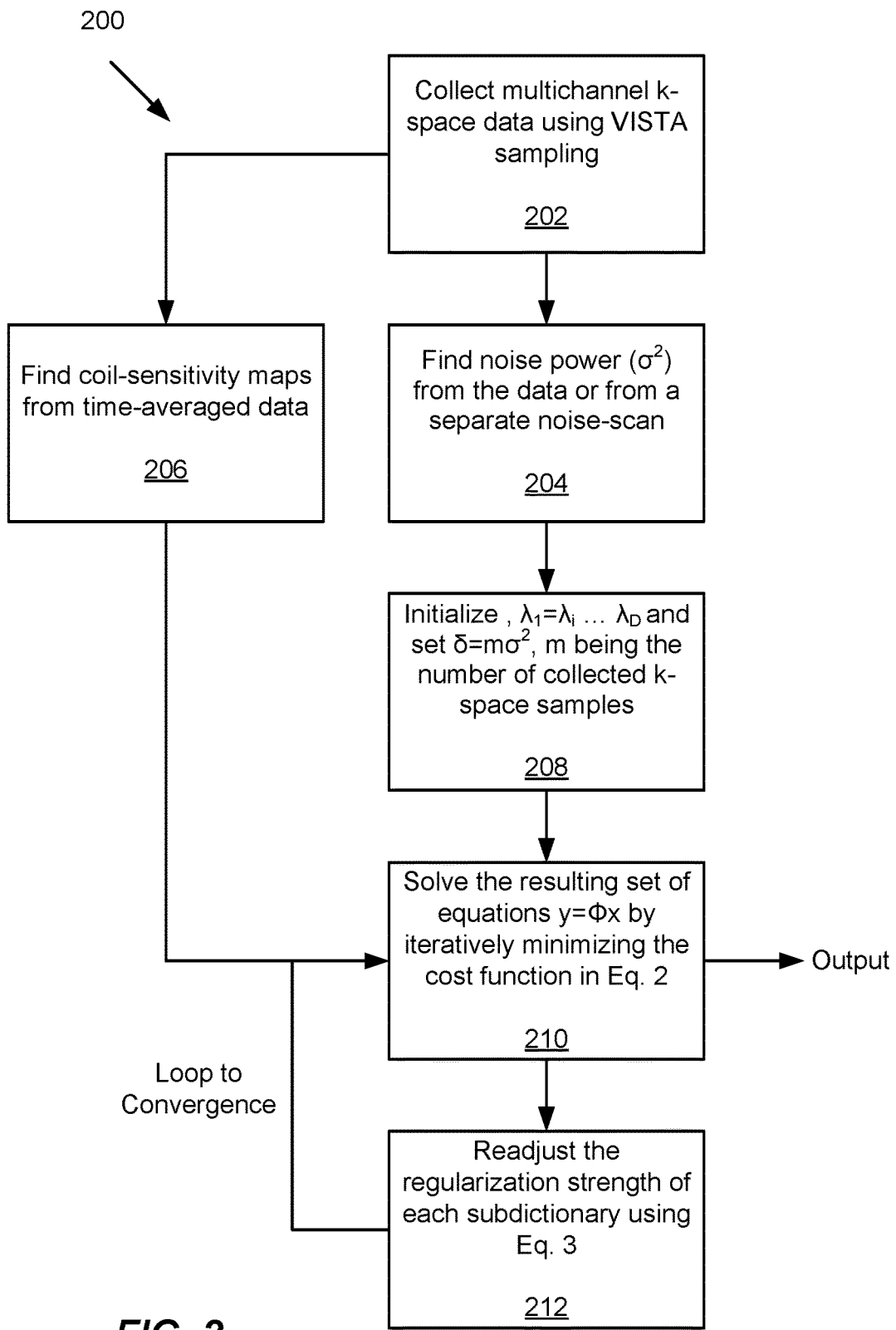
FIG. 2 is an example operational flow in accordance with the present disclosure.

FIG. 2 illustrates an example operation flow 200 for acquiring and processing image data. At 202, multichannel k-space data is collected using VISTA sampling. This may be accomplished using techniques described in U.S. patent application Ser. No. 14/593,322, filed Jan. 9, 2015, entitled "VARIABLE DENSITY INCOHERENT SPATIOTEMPORAL ACQUISITION (VISTA) FOR HIGHLY ACCELERATED MAGNETIC RESONANCE IMAGING," which is incorporate herein by reference in its entirety. At 204, a noise power ($\sigma^2$) from the data or from a separate noise-scan is determined. In parallel, at 206, coil-sensitivity maps from time-averaged data are determined. At 208, the relative weights $\lambda_1 = \lambda_2 = \ldots = \lambda_D$=constant are initialized and $\delta = m\sigma^2$ is set, with m being the number of collected k-space samples. At 210, the results from 206 and 208 are used to solve the resulting set of equations y=φx by iteratively minimizing the cost function in Eq. 2, above. At 212, After every $n^{th}$ iteration, the regularization strength of each subdictionary is readjusted using Eq. 3. The process loops back to 210 until convergence is found, after which the result is output.

Simulated Results

SCoRe was evaluated using a 120×120 dynamic digital phantom with 48 temporal frames. The phantom consisted of both dynamic and static ellipses and a static rectangle. To emulate experimental conditions, twelve uniformly spaced circular receive coils were simulated around the phantom. The data was undersampled at R=4, 8, 12, and 15 using VISTA sampling. In the simulation, real-time cardiac cine data were acquired with VISTA (3T Siemens, 32 channel cardiac array) at four different acceleration rates (R=4, 8, 12, and 15) from a healthy volunteer. The acquisition was carried out under free-breathing conditions in both short-axis and 4-chamber orientations. Other imaging parameters included: 48 frames, 224×144 matrix size, 360×288 mm2 FOV, SSFP sequence, TE of 1 ms, TR of 2.7 ms, and flip angle 60°. For both the simulation and experimental data, we used 3D UWT of the spatiotemporal image for $\Psi$. For the traditional approach, all eight subbands of UWT were treated identically (Eq. 1). For SCoRe, the subband weights ($\lambda_i$) were estimated using Eq. 3. In a SENSE-based implementation, the coil sensitivity maps were estimated from fully sampled, time-averaged data.

Figure 3A:
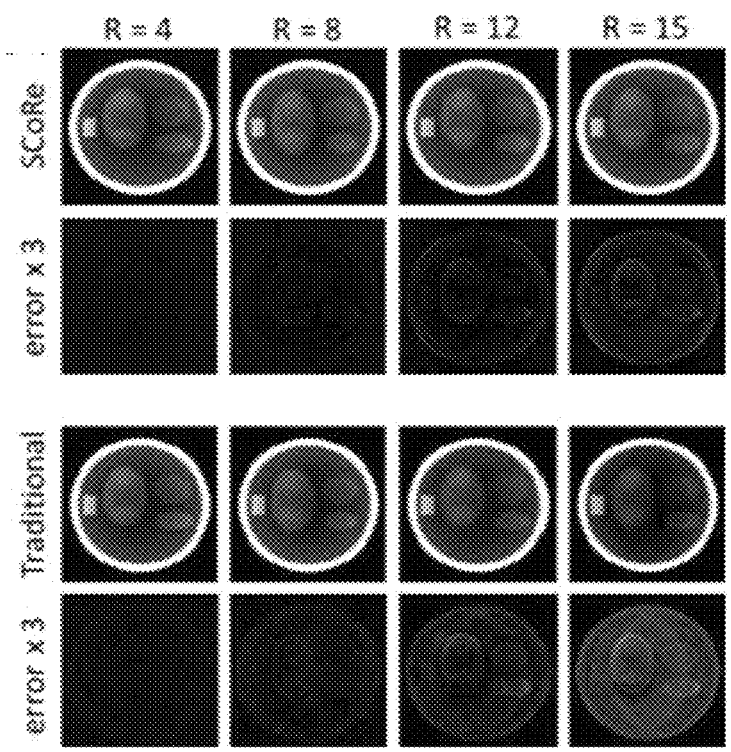
FIGS. 3A, 3B and 4 show results of simulated data derived using the operation flow of FIG. 2.
Figure 3B:
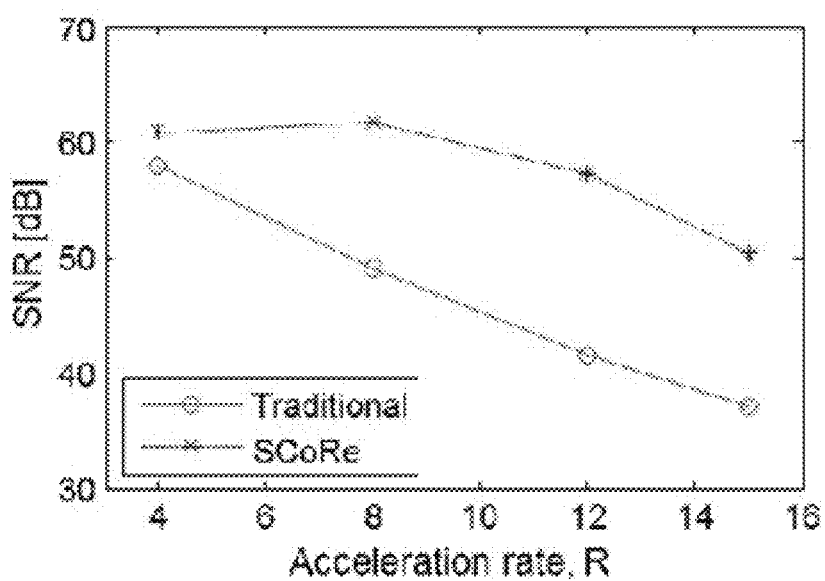
Figure 4:
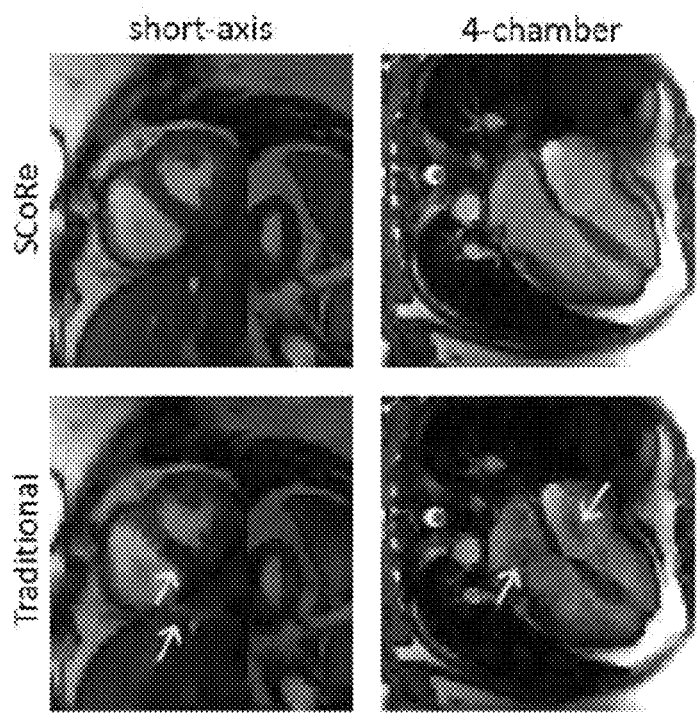

FIGS. 3A, 3B and 4 show results of simulated data derived using the operational flow 200 of FIG. 2. FIG. 3A shows the phantom results from one of the 48 frames. SCoRe generated images with higher recovery SNR (−20 log (x−x̂/x)) and lower visible artifacts. The difference between the traditional approach and SCoRe was more pronounced at higher acceleration rates. At rate 15, SCoRe had 15 dB higher recovery SNR. FIG. 2A also shows amplified error images. FIG. 3B shows recovery SNR as function of acceleration rate.

FIG. 4 shows results from free-breathing, real breathing MRI at rate 12. As evident from the representative frames, SCoRe suppressed aliasing artifacts that are visible in the traditional processing. For SCoRe, the computation time for phantom and in vivo datasets was approximately 3 to 5 minutes per dataset.

Validation Using Simulated Lowfield Data

To validate the operation of the MRI apparatus 100, low field (0.5 T) data were simulated by adding noise to the data collected using 1.5 T or 3.0 T systems to provide a conservative estimate of low field performance accounting for the non-ideal modeling encountered with high field measurements. The results indicate the real-time cine and flow imaging are feasible at lower field strengths.

Real-Time Cine

The following parameters were used to validate real-time cine.

Figure 5:
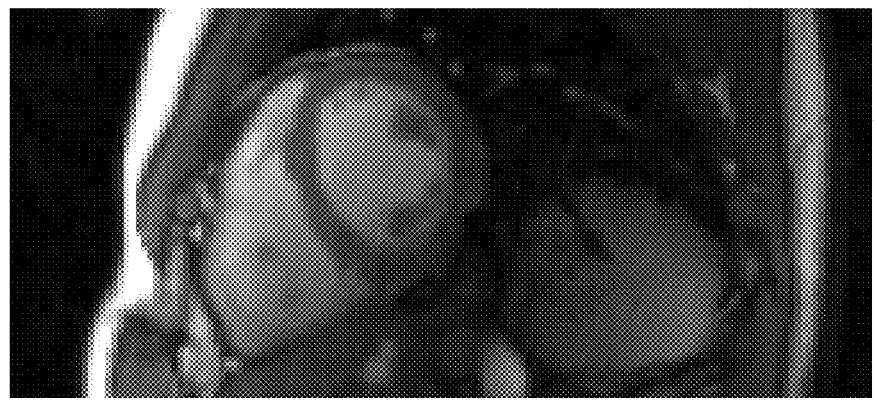
FIG. 5 illustrates a comparison of 0.5 T simulated real-time cine images with 3 T images.
Figure 5:
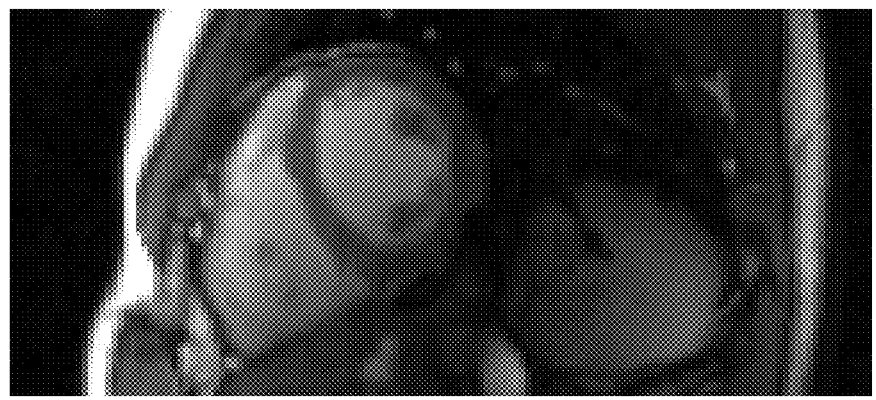

Subject: A healthy volunteer scanned on 3T
Pulse sequence: SSFP
FOV: 360×288 mm$^2$
Matrix: 224×144
Slice thickness: 8 mm
TE/TR: 1.0/2.8 ms
Acceleration: 8 (50 ms temporal resolution)
Coil array: 32 channel body coil array
Sampling: VISTA
Reconstruction: SCoRe as described above
Noise: separate noise scan FIG. 5 shows a comparison of the reconstructed images for real-time cine for 3T and simulated 0.5 T field strengths. As shown, the images created from the simulated 0.5T data compare favorably with the images created from 3T data.

2D FLOW

The following parameters were used to validate 2D Flow.

Figure 6:
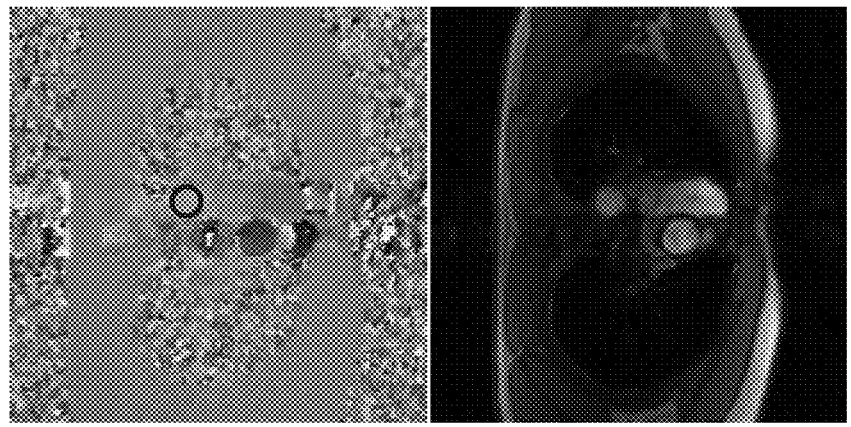
FIG. 6 shows a comparison of the mean and peak velocity vs. cardiac phase for 1.5 T and simulated 0.5 T field strengths.
Figure 6:
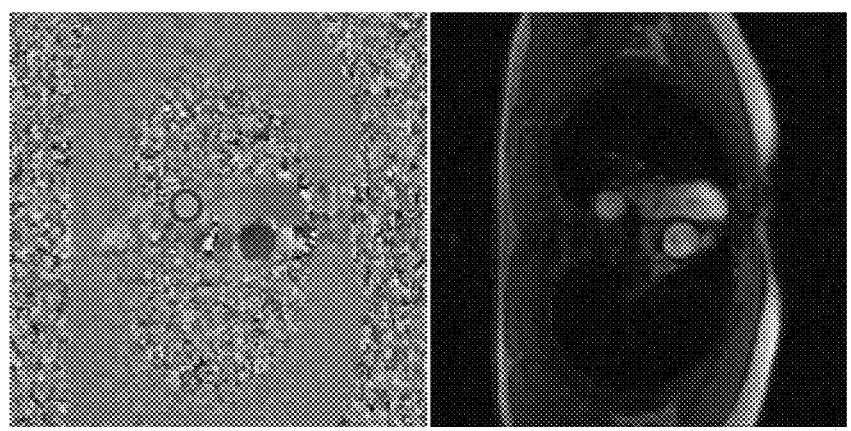
Figure 7:
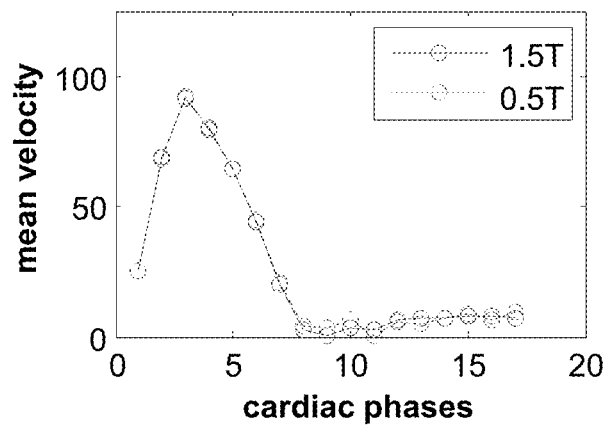
FIG. 7 illustrates a comparison of 0.5 T simulated 2D flow images with 1.5 T images.
Figure 7:
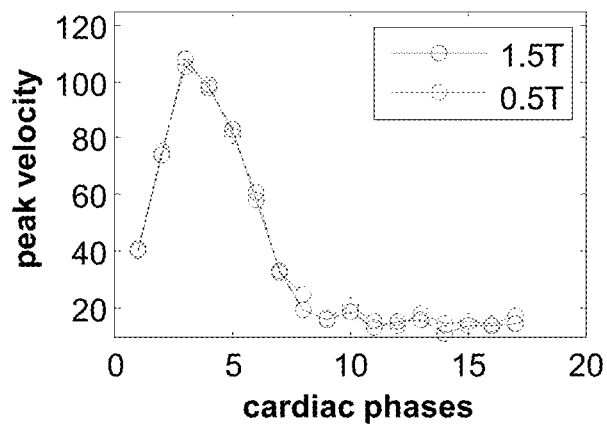

Subject: A healthy volunteer scanned on 1.5 T
Pulse sequence: SSFP
FOV: 360×288 mm$^2$
Matrix: 224×144
Slice thickness: 8 mm
TE/TR: 1.0/2.8 ms
Acceleration: 8 (50 ms temporal resolution)
Coil array: 32 channel body coil array
Sampling: VISTA
Reconstruction: SCoRe as described above
Noise: separate noise scan FIG. 6 shows a comparison of the reconstructed images for 2D Flow for 1.5 T and simulated 0.5 T field strengths. As shown, the images created from the simulated 0.5 T data compare favorably with the images created from 1.5 T data. FIG. 7 shows a comparison of the mean and peak velocity vs. cardiac phase for 1.5 T and simulated 0.5 T field strengths for the region-of-interest drawn in FIG. 6. The results for the simulated 0.5 T field strength data track closely with the 1.5 T field strength data.

Thus, the technological advances disclosed herein are effective for time-series of images, i.e., for "dynamic imaging" which is relevant to cardiac MRI. Other CMR applications, including first pass perfusion, MR angiography, and late gadolinium enhancement are expected to perform as well at low field using SA data processing methods. Still further, the MRI apparatus described herein may be used for other imaging applications.

It should be understood that the various techniques described herein may be implemented in connection with hardware or software or, where appropriate, with a combination of both. Thus, the methods and apparatus of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computer, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A method for reconstructing image data, comprising:
acquiring multichannel k-space data;
determining a noise power of the k-space data;
determining coil-sensitivity maps;
initializing values of relative weights that are respectively applied to subdictionaries used to model an image;
iteratively minimizing a weighted $l_1$-norm of image representation in subdictionaries in accordance with the relative weights while constraining a residual norm of a data-fidelity term based on the determined noise power;
updating, within each iteration, the relative weights of the subdictionaries based on a subdictionary-specific maximum likelihood fitting of coefficient distributions with a Laplacian; and
outputting reconstructed images upon convergence of a cost function used to estimate the reconstructed images.

2. The method of claim 1, wherein the acquiring is performed using variable density incoherent spatiotemporal acquisition (VISTA).

3. The method of claim 1, wherein unconstrained optimization routines are used to minimize the cost function.

4. The method of claim 1, wherein subdictionaries are subbands of decimated or non-decimated wavelet decomposition.

5. The method of claim 1, wherein subdictionaries are disparate transforms.

6. The method of claim 1, wherein a measurement matrix is used that is based on GRAPPA or SPIRiT.

7. The method of claim 1, wherein the noise power is estimated from the k-space data or from separate noise scan.

8. The method of claim 1, wherein the relative weights of the subdictionaries weights are estimated less frequently than every iteration.

9. The method of claim 1, wherein single receive coil is used for acquisition.

10. The method of claim 1, wherein data is collected from low-field MRI scanner.

11. The method of claim 1, further comprising determining an uncertainty map of pixel values in the reconstructed images.

12. A low-field magnetic resonance imaging (MRI) apparatus, comprising:
a scanner that generates a magnetic field within a predetermined measurement space, the magnetic field having a field strength of approximately 0.5 Tesla (T);
a controller;

a receiver that receives and stores MR data associated with a measured volume; and an evaluation module, that executes on the controller, that prepare the MR data such that the MR data can be graphically presented on a monitor, the evaluation module executing instructions that cause the controller to determine coil-sensitivity maps; initialize values of relative weights that are respectively applied to subdictionaries used to model an image;

iteratively minimize a weighted $l_1$-norm of image representation in subdictionaries in accordance with the relative weights while constraining a residual norm of a data-fidelity term based on a determined noise power; update, within each iteration, the relative weights of the subdictionaries based on a subdictionary-specific maximum likelihood fitting of coefficient distributions with a Laplacian; and output reconstructed images upon convergence of a cost function used to estimate the reconstructed images.

13. The MRI apparatus of claim 12, the scanner further comprising an 18 coil array.

14. The MRI apparatus of claim 12, wherein images are acquired using one of SPIRiT, GRAPPA, SENSE, VISTA, AMP, FISTA, SCoRE, and/or Bayesian Inference.

15. The MRI apparatus of claim 12, wherein the apparatus is a cardiac magnetic resonance (CMR) apparatus.

* * * * *